(12) United States Patent
Herbig et al.

(10) Patent No.: US 11,610,416 B2
(45) Date of Patent: Mar. 21, 2023

(54) DEVICE FOR IMAGE-BASED CELL CLASSIFICATION, METHOD THEREFOR AND USE THEREOF

(71) Applicants: Max-Planck-Gesellschaft zur Förderung der Wissenschaften e.V., Munich (DE); Technische Universität Dresden, Dresden (DE)

(72) Inventors: Maik Herbig, Dresden (DE); Ahmad Ahsan Nawaz, Dresden (DE); Martin Nötzel, Dresden (DE); Jochen Guck, Leipzig (DE)

(73) Assignees: TECHNISCHE UNIVERSITÄT DRESDEN, Dresden (DE); MAX-PLANCK-GESELLSCHAFT ZUR FÖRDERUNG DER WISSENSC, Munich (DE)

( * ) Notice: Subject to any disclaimer, the term of this patent is extended or adjusted under 35 U.S.C. 154(b) by 0 days.

(21) Appl. No.: 17/018,033

(22) Filed: Sep. 11, 2020

(65) Prior Publication Data

US 2021/0089751 A1    Mar. 25, 2021

(30) Foreign Application Priority Data

Sep. 23, 2019  (EP) .................................... 19198891

(51) Int. Cl.
*B01L 3/00* (2006.01)
*G01N 21/85* (2006.01)
(Continued)

(52) U.S. Cl.
CPC ...... *G06V 20/698* (2022.01); *B01L 3/502761* (2013.01); *G01N 21/85* (2013.01);
(Continued)

(58) Field of Classification Search
CPC .. G06K 9/00147; G01N 21/85; G01N 33/487; B01L 2200/0652; G02K 9/6256
See application file for complete search history.

(56) References Cited

U.S. PATENT DOCUMENTS 7,270,986 B2    9/2007  Mutz et al.
2017/0333903 A1* 11/2017 Masaeli ............ B01L 3/502761
(Continued)

FOREIGN PATENT DOCUMENTS

EP      3036520 B1     7/2017
WO   WO 2007/006322 A1   1/2007
(Continued)

OTHER PUBLICATIONS

Eulenberg et al., Reconstructing cell cycle and disease progression using deep learning. Nat Commun. Sep. 6, 2017;8(1):463. doi: 10.1038/s41467-017-00623-3.
(Continued)

*Primary Examiner* — Michael McCullough
*Assistant Examiner* — Jessica L Burkman
(74) *Attorney, Agent, or Firm* — Troutman Pepper Hamilton Sanders LLP

(57) ABSTRACT

A classifying device for classifying cells in real-time, comprising: as alignment unit configured to align a cell to be classified along the cell's major axis; and a classifying unit configured to classify the aligned cell using a multilayer perceptron, MLP; wherein the MLP classifies the aligned cell based on one or more images of the aligned cell. By executing the classifying device, an improved and efficient cell classification in real-time based on cell images can be provided, while labelling of the cells to be classified can be avoided.

17 Claims, 6 Drawing Sheets

(51) Int. Cl.
  *G01N 33/487* (2006.01)
  *G06K 9/62* (2022.01)
  *G06V 20/69* (2022.01)

(52) U.S. Cl.
  CPC ......... *G01N 33/487* (2013.01); *G06K 9/6256* (2013.01); *B01L 2200/0652* (2013.01)

(56) References Cited

U.S. PATENT DOCUMENTS

2019/0384963 A1* 12/2019 Kim ................... G06T 7/248
2021/0209337 A1* 7/2021 Ozcan ................ G01N 15/1484

FOREIGN PATENT DOCUMENTS

| WO | WO 2010/024753 A1 | 3/2010 |
| WO | WO 2010/065868 A2 | 6/2010 |
| WO | WO 2010/123453 A1 | 10/2010 |
| WO | WO 2012/027366 A2 | 3/2012 |
| WO | WO 2012/114076 A1 | 8/2012 |
| WO | WO 2012/135663 A2 | 10/2012 |
| WO | WO 2013/116311 A1 | 8/2013 |
| WO | WO 2014/022268 A1 | 2/2014 |
| WO | WO 2015/058265 A1 | 4/2015 |
| WO | WO 2016/025518 A1 | 2/2016 |
| WO | WO 2016/179664 A1 | 11/2016 |
| WO | WO 2017/035287 A1 | 3/2017 |
| WO | WO 2017/082828 A1 | 5/2017 |

OTHER PUBLICATIONS

Herbig et al., Label-free detection of rod precursor cells using artificial intelligence. Retina Conference. Postdam, Germany. Mar. 23, 2019. Poster. 1 page.
Herbig et al., Label-free detection of rod precursor cells using artificial intelligence. Retina Conference. Postdam, Germany. Mar. 23, 2019. Abstract Only. 1 page.
Isozaki et al., A practical guide to intelligent image-activated cell sorting. Nat Protoc. Aug. 2019;14(8):2370-2415. doi: 10.1038/s41596-019-0183-1. Epub Jul. 5, 2019.
Nitta et al., Intelligent Image-Activated Cell Sorting. Cell. Sep. 20, 2018;175(1):266-276.e13. doi: 10.1016/j.cell.2018.08.028. Epub Aug. 27, 2018.
Otto et al., Real-time deformability cytometry: on-the-fly cell mechanical phenotyping. Nat Methods. Mar. 2015;12(3):199-202, 4 p following 202. doi: 10.1038/nmeth.3281. Epub Feb. 2, 2015.
Rosendahl et al., Real-time fluorescence and deformability cytometry. Nat Methods. May 2018;15(5):355-358. doi: 10.1038/nmeth.4639. Epub Apr. 2, 2018.
Bishop, Invariances. In: Pattern Recognition and Machine Learning. 2006. Jordan et al., Eds. Springer Science+Business Media, LLC, New York. Chapter 5.5.3:261-3.
Fasel et al., Rotation-Invariant Neoperceptron. IEEE Xplore. Proceedings of the 18th International Conference on Pattern Recognition (ICPR). 2006;3:336-9. doi: 10.1109/ICPR.2006.1020.
Greenberg et al., Rotation-invariant MLP classifiers for automatic aerial image recognition. Eighteenth Convention of Electrical and Electronics Engineers in Israel. Jul. 8, 1995;2.2.4/1-2.2.4/5. doi: 10.1109/EEIS.1995.513798.
Rowley et al., Neural network-based face detection. IEEE Transactions on Pattern Analysis and Machine Intelligence. Jan. 1998;20(1)23-38. doi: 10.1109/34.655647.

* cited by examiner

DEVICE FOR IMAGE-BASED CELL CLASSIFICATION, METHOD THEREFOR AND USE THEREOF

CROSS REFERENCE TO RELATED APPLICATION

This application claims priority to European Application No. 19 198 891.4, filed Sep. 23, 2019, the entire contents of the aforementioned application is hereby incorporated herein by reference.

The present invention relates to image-based cell classification. In particular, the present invention relates to a classifying device and a classifying method for classifying cells in real-time and to a sorting device and sorting method for sorting cells in real-time. It also relates to uses of these devices.

BACKGROUND OF THE INVENTION

In the field of biological, biotechnological, or medical procedures, the classification and sorting of cells from a heterogeneous population is often necessary before further analysis of cells is possible. The sorted cells can, for example, be subjected to subsequent refined analysis and inquiry into their proteomic, transcriptomic, or genetic identity and function or can be used for culture and serve the establishment of specific drugs. These sorted cells may also be transplanted into patients in regenerative medical applications.

Conventional classifying and sorting approaches rely on fluorescent or magnetic properties conferred to molecular markers used for passive or active separation. Such labelling must be applied to cell surfaces or into cells via dyes, antibodies or genetic modification. Then this labelling can be detected by flow cytometry and cells can be sorted by fluorescence-activated cell sorting (FACS) devices. However, such labeling is time- and cost-intensive, could alter cellular properties and function, and might be incompatible with subsequent use, for example in transplantation.

Currently, there are no alternatives given which ensure classification and sorting of cells with high throughput (for example more than 50 cells per second) but without prior staining/labelling. For example, bright-field images of cells often show obvious differences which could be used for classification and sorting. However, so far there are no efficient techniques given which evaluate images of cells in real-time in order to be able to classify these cells and to control a sorting unit on a cytometer. The fastest realization of this kind of classification and sorting technique so far solely reaches latencies of 30 ms and usually uses fluorescence images.

Therefore, the aim of the present invention is to solve the problem concerning efficient cell classification and sorting based on cell images without the use of cell labelling. In particular, the present invention proposes a classifying device and a classifying method for classifying cells in real-time and a sorting device and sorting method for sorting cells in real-time, wherein classification of label-free, i.e. marker-free, cells based on images with high throughput is to be guaranteed.

SUMMARY OF THE INVENTION

It is desired to provide means for improved, efficient, and accurate classification of label-free and marker-free cells based on cell images, like bright-field images, with high throughput.

At least some of the mentioned objects and drawbacks are solved by the subject matter of the independent claims. Further preferred embodiments are defined in the dependent claims.

According to one aspect of the present invention, a classifying device for classifying cells in real-time comprises an alignment unit configured to align a cell to be classified along the cell's major axis; and a classifying unit configured to classify the aligned cell using a multilayer perceptron (MLP), wherein the MLP classifies the aligned cell based on an image of the aligned cell. Accordingly, an improved, efficient, and accurate classification of cells in real-time based on images of the cells with high throughput can be provided.

According to another aspect of the present invention, a sorting device comprising the above stated classifying device further comprises a sorting unit configured to sort the classified cell to a target outlet or to a default outlet based on a classification result output by the classifying device. Accordingly, improved, efficient, and accurate sorting of cells in real-time based on images of the cells with high throughput can be provided.

According to another aspect of the present invention, a classifying method for classifying cells in real-time comprises the steps of aligning a cell to be classified along the cell's major axis; and classifying the aligned cell using a multilayer perceptron, MLP, wherein the MLP classifies the aligned cell based on an image of the aligned cell. Accordingly, an improved, efficient, and accurate classification of cells in real-time based on images of the cells with high throughput can be provided.

According to another aspect of the present invention, a sorting method comprising the steps of the above stated classifying method further comprises the step of sorting the classified cell to a target outlet or to a default outlet based on a classification result of the classifying method. Accordingly, improved, efficient, and accurate sorting of cells in real-time based on images of the cells with high throughput can be provided.

Further advantageous features of the invention are disclosed in the appended claims.

DETAILED DESCRIPTION

Preferred embodiments of the invention are described with reference to the figures. It is noted that the following description contains examples only and should not be construed as limiting the invention. In the following, similar or same reference signs indicate similar or same elements or functions.

Figure 1:
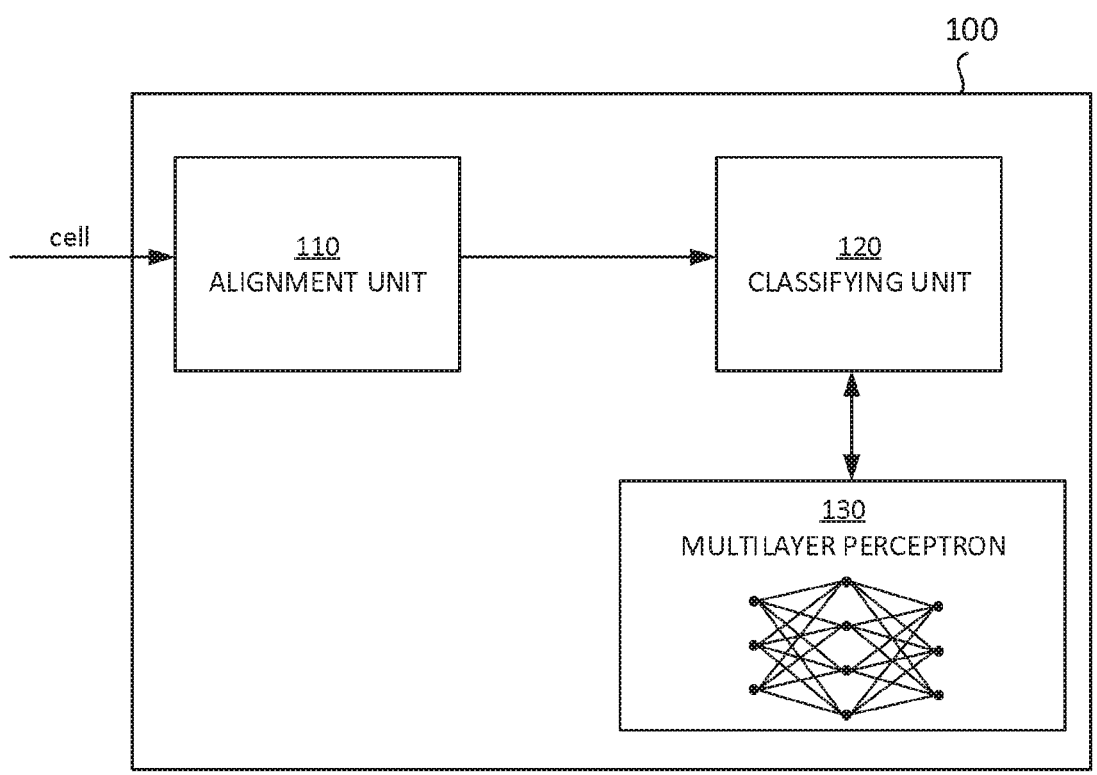
FIG. 1 is an illustration of a classifying device according to an embodiment of the present invention.

FIG. 1 is an illustration of a classifying device 100 according to an embodiment of the present invention. The classifying device for classifying cells in real-time comprises an alignment unit 110 and a classifying unit 120 which uses a multilayer perceptron 130 for cell classification. The alignment unit 110, the classifying unit 120, and the MLP 130 are described in more detail below with reference to FIG. 1.

The alignment unit 110 receives cells to be classified and aligns each cell along the cell's major axis. For example, the alignment unit 110 comprises a microfluidic channel through which the cells to be classified flow. Due to forces being present inside the microfluidic channel and being applied on the cells flowing through the microfluidic channel, each cell is automatically aligned along its major axis.

Then, the classifying unit 120 classifies the aligned cells using the MLP 130. The MLP 130 is a class of feedforward artificial neural network which classifies the aligned cells based on images of the aligned cells. The images of the aligned cells may be images of marker-free cells in order to avoid time- and cost-intensive labelling and alteration of cellular properties and function due to labelling. In addition, by first aligning each cell along its major axis and then classifying the aligned cell based on cell images, a fast and accurate classification can be ensured using the MLP 130 due to standardized cell images.

Figure 2A:
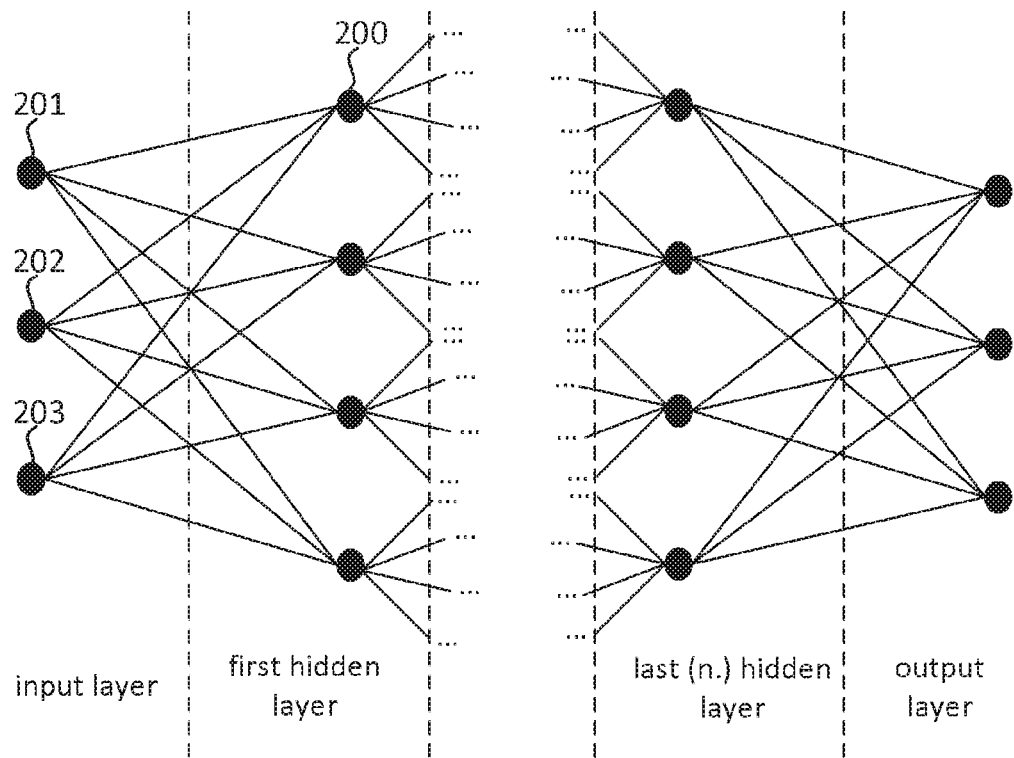
FIGS. 2A and 2E show a general multilayer perceptron used for classification.
Figure 2B:
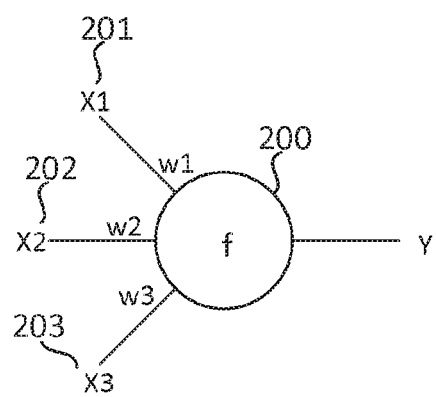

The MLP 130 is explained in more detail with reference to FIGS. 2A and 2B. FIG. 2A shows the MLP 130 as a general multilayer perceptron used for classification, while FIG. 2B shows a node 200 of the first hidden layer for further details.

As already stated above, the MLP 130 belongs to the general class of feedforward neural networks comprising an input layer, at least one hidden layer, and an output layer. In particular, the MLP 130 may comprise an input layer having at least one neuron, one or several hidden layers, each hidden layer usually having multiple neurons, and an output layer having again at least one neuron. In this matter, a neuron is a node of the neural network, wherein a collection of neurons, i.e. nodes, forms a layer, for example, an input layer, a hidden layer, or an output layer. In FIG. 2A, the input layer and the output layer each include three neurons, respectively. However, this is only illustrative, and the input layer and output layer of the MLP 130 may comprise more or less neurons depending on the configuration.

In addition, two hidden layers are illustrated in FIG. 2A, wherein the first hidden layer has four neurons and the last hidden layer has four neurons. However, the MLP 130 can also only comprise one hidden layer or several additional hidden layers may be given between these two hidden layers. Again, the number of hidden layers and the number of neurons for each hidden layer are only illustrative, and each hidden layer can have more or less neurons, the number of neurons for each hidden layer can vary depending on the configuration.

A neuron of the input layer provides information from the outside world to the MLP 130, wherein no computation is performed in any of the neurons of the input layer. The input layer solely passes on the information to the neurons in the hidden layer(s). In the embodiment of the present invention, images of cells to be classified are input as information to the input layer of the MLP 130. For example, the images of the cells used for classification are bright-field images of the cells. However, other types of imaging such as dark field imaging or an analysis of diffraction images of the cells are also possible. It is particularly preferred to use quantitative phase imaging (also known as "quantitative phase-contrast microscopy"). This imaging method allows obtaining a measure of the density distribution inside the cells and hence provides more input data for the MLP. Accordingly, a particularly good classification is possible. Other imaging methods such as Raman imaging, Brillouin imaging, diffraction interferometry and phase contrast microscopy are also envisaged. It should also be understood that the above list is non-exhaustive. As the input to the MLP 130 is an image, the number of neurons in the input layer may equal the number of pixels of the image input to the MLP 130. For example, if pixel images between 20×20 and 50×50 are used for classification, it means between 400 and 2500 neurons are provided in the input layer.

The neurons of the hidden layer have no direct connection with the outside world, such that the neurons are called "hidden". These neurons perform computations and transfer information from the neurons of the input layer to the neurons of the output layer. A collection of hidden neurons forms a hidden layer, wherein the MLP 130 may comprise one hidden layer between the input layer and the output layer, or may comprise more than one hidden layer depending on the complexity of the input data, i.e. the images of the cells to be classified, and the MLP.

The output layer is responsible for computing the end result. Depending on the cell images input to the MLP 130 and the process of the at least one hidden layer of the MLP 130, the output layer is able to output classification results for the corresponding cells. The number of neurons in the output layer may equal the number of classes the MLP 130 should predict. For example, when the MLP 130 receives images of white blood cells or red blood cells, the output layer is able to output classification results showing whether the cell is a white blood cell or a red blood cell. In this example, a first class refers to white blood cells and a second class refers to red blood cells and thus the output layer may comprise two neurons to differentiate between white blood cells and red blood cells. To give another example, it may be furthermore desired to classify red blood cells, healthy white blood cells and cancerous white blood cells using the MLP 130 which results in three classes (class 1: red blood cells; class 2: healthy white blood cells; class 3: cancerous white blood cells). Hence, the output layer of the MLP 130 may comprise three neurons. In summary, the MLP 130 can differentiate between different types of cells based on their cell images.

In other words, each neuron may receive input from some other nodes or from an external source and may compute an output. Each neuron may have an associated neutral, positive, or negative weight w and each layer may apply a function f to the inputs to calculate its output. The function f may be non-linear and may be called activation function. The purpose of the activation function is to introduce non-linearity into the output of a neuron to represent data received by the input layer and processed by the MLP 130. There are several activation functions given in the prior art (rectifier, linear, sigmoid, hyperbolic tangent, softmax, etc.) which may be chosen depending on the configuration and purpose of the MLP 130.

FIG. 2B is an illustration of a neuron 200 of the MLP 130 illustrated in FIG. 2A. In this case, the neuron 200 is a hidden neuron of the first hidden layer of the MLP 130 of FIG. 2A and is connected to three neurons 201, 202, and 203 of the input layer of the MLP 130 of FIG. 2A. The neuron 200 receives three input values X1, X2, and X3 from the neurons 201, 202, and 203, wherein each input is associated with one of the weights w1, w2, and w3. The neuron 200 then applies the activation function f to calculate its output Y. The activation function f may use as inputs the weighted sum of its inputs as shown below:

$$Y=f(w1*X1+w2*X2+w3*x3).$$

The neuron 200 then outputs its calculated output Y to the neurons of the subsequent layer to which the neuron 200 is connected. In this case, the neuron 200 may output its calculated output Y to neurons of the second hidden layer to which the neuron 200 is connected for further processing.

Training the MLP 130 means calibrating the weights w associated with the inputs of the neurons. In the beginning, initial weights may be randomly selected based on, for example, Gaussian distribution. The process for training the MLP 130 may then be repeated multiple times on the initial weights until the weights are calibrated using a backpropagation algorithm to accurately predict an output.

In the embodiment of the present invention, the MLP 130 is trained on an input-output pair, the input being images of cells and the output being corresponding classification results. For example, for training the MLP 130, data of a database storing multiple cell images and corresponding classification results for the cells may be used. If, for example, white and red blood cells are to be classified, the MLP 130 is trained on several input-output pairs, the input being images of white and red blood cells and the output being the corresponding classification result of having a white blood cell or a red blood cell. Once the MLP 130 has been trained, the MLP 130 can be used for new cell images for which no classification result is known yet. If, for example, bright-field images of cells should be used for classification, the MLP 130 is also trained on bright-field images of cells.

To obtain an MLP 130 that is able to accurately and correctly classify cell images, the MLP 130 may be trained on several input-output pairs and the training process may be repeated several times. In this matter, the training phase may take several minutes to several hours depending on the number of input-output pairs and the desired accuracy of the MLP 130 for classification. However, by providing an aligning unit 110 before classifying the cells and by using the cell images of aligned cells, the cell images are standardized resulting in a shorter training process and in a more accurate and correct cell classification. Thus, cell classification in real-time with high throughput and no cell labelling is possible.

In FIG. 1, the classifying unit 120 and the MLP 130 are shown as separate entities. For example, the classifying device 100 is a common computing device, wherein the MLP 130 is stored in a storage or memory of the computing device and the classifying unit 120 is implemented as a processing device being able to access the MLP 130 in the storage in order to obtain classification results based on cell images. However, the classifying device 100 is not limited to this setup and the MLP 130 may also be integrated into the classifying unit 120.

Figure 3:
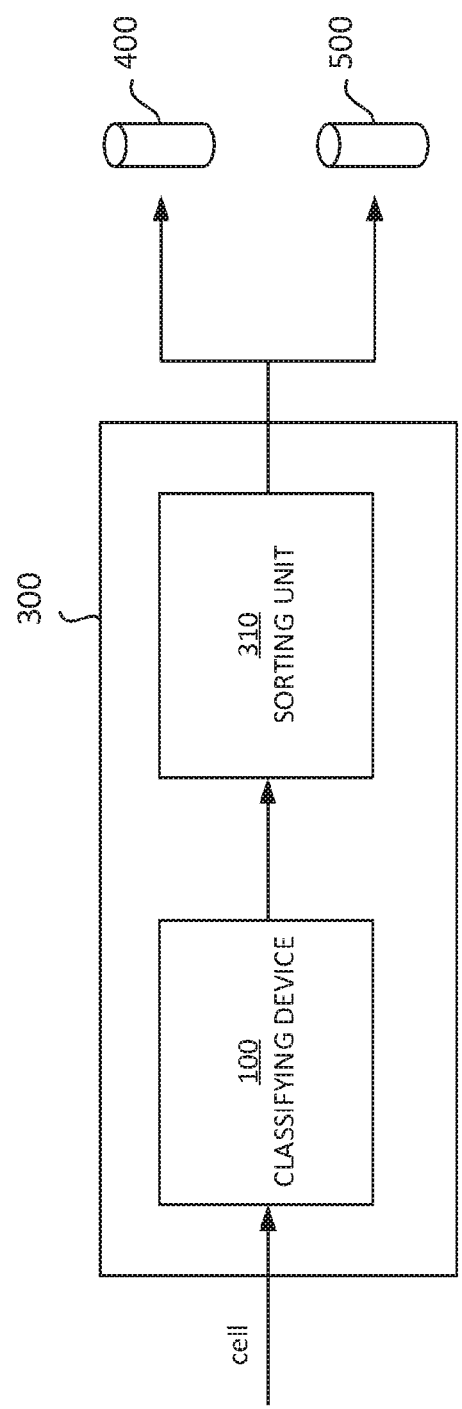
FIG. 3 is an illustration of a sorting device according to another embodiment of the present invention.

FIG. 3 is an illustration of a sorting device according to another embodiment of the present invention. The sorting device may comprise the classifying device 100 and a sorting unit 310. As the classifying device 100 has been described in much detail above with reference to FIG. 1, a detailed description of the classifying device 100 at this point is omitted for conciseness reasons.

The sorting unit 310 may obtain the classification result output by the classifying device 100 and may sort the respective cell to a target outlet 400 or to a default outlet 500 based on the obtained classification result. For example, a sample may contain white and red blood cells, wherein the white blood cells are needed for further analysis. In this example, if cells in the sample are to be classified and sorted to obtain the white blood cells for further analysis, the classifying device 100 classifies cells based on their cell images into white and red blood cells and outputs the results to the sorting unit 310. The sorting unit 310 then sorts the white blood cells to the target outlet 400 and the red blood cells to the default outlet 500. The setup is not limited to solely one target outlet and the setup may also contain more than one target outlet depending on the number of different target cells. Another option may be to provide a stepwise setup for classification, wherein cells are classified using target outlets and default outlets arranged in various stages. In this stepwise setup, the cells already being sorted to a target outlet or the default outlet may be passed on to another outlet, either target outlet or default outlet, resulting in a gradual and more refined classification.

The sorting unit 310 may use standing or travelling surface waves within the acoustic wavelength range in order to separate the classified cells and either push a cell to a target outlet 400 or to a default outlet 500. The target outlet 400 and the default outlet 500 may be a test tube or any other container for collecting the classified cells of a sample.

Figure 4:
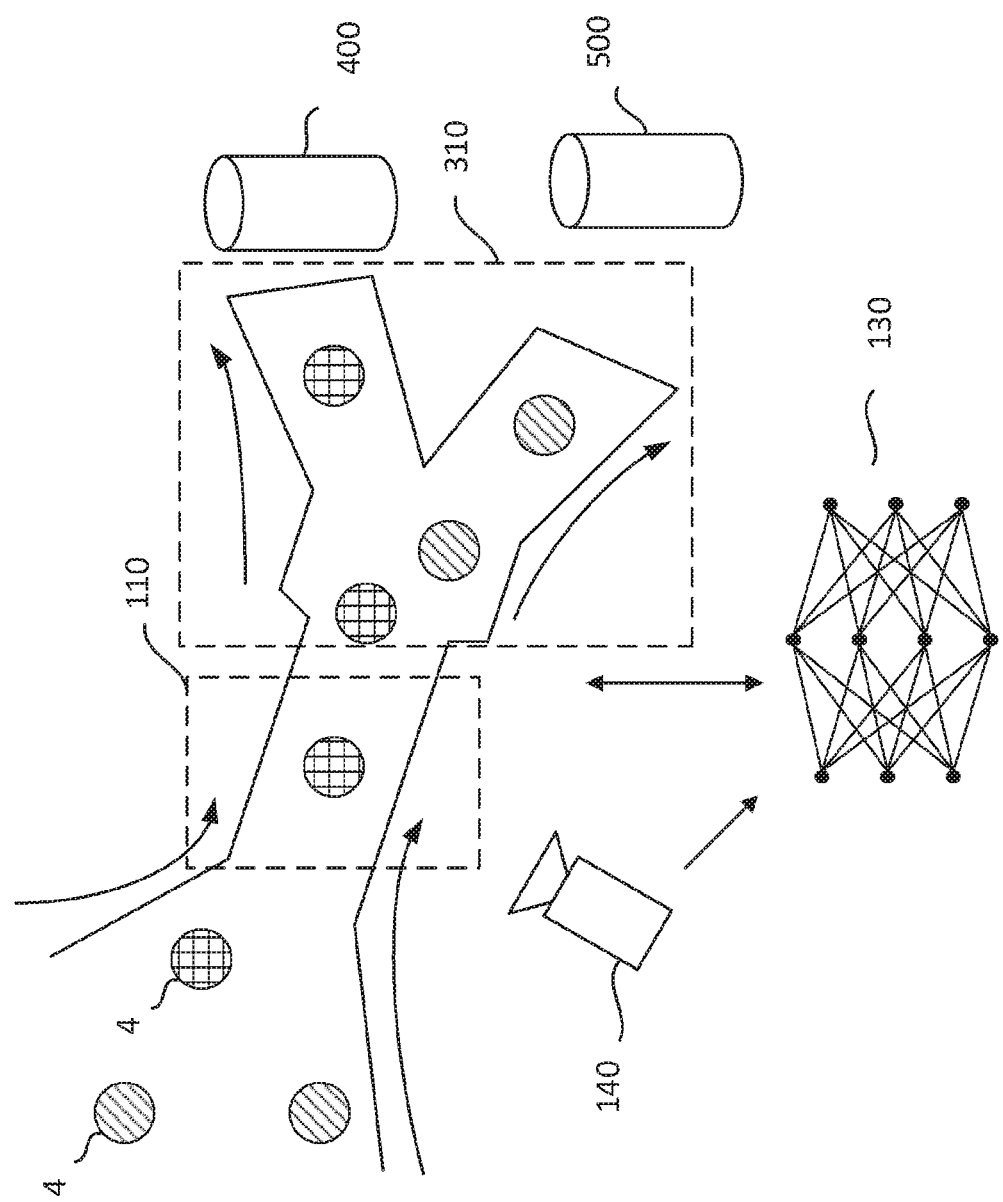
FIG. 4 shows an example of a setup for classifying and sorting cells according to an embodiment of the present invention.

FIG. 4 shows an example of a setup for classifying and sorting cells according to an embodiment of the present invention. For the setup, the system described in WO 2015/024690 A1 may be used which is sold under the name "AcCellerator" by Zellmechanik Dresden GmbH. The "AcCellerator" is a high-speed imaging cytometer for mechanical cell characterization through real-time deformability cytometry measurement. FIG. 4 shows two types of cells 4 (chequered and striped) in a heterogeneous sample, wherein the chequered cells may be white blood cells and the striped cells may be red blood cells. The cells 4 do not have to be red and white blood cells but can be any type of cells. In addition, the number of different types of cells does not have to be two, and more types of cells may be present in the heterogeneous sample.

As shown in FIG. 4 the cells 4 may be inserted into the setup and may flow from left to right (see the arrows shown in FIG. 4). To ensure that the cells flow through the setup, a pump (for example neMESyS 290N produced by Cetoni GmbH, Korbussen) may be used. As the tubing, products by DuPont®, FEP Fluoropolymer tubings (Postnova Analytics GmbH, Landsberg) were used.

First of all, the cells 4 may one at a time reach the alignment unit 110 which has been described in much detail above. For example, the alignment unit 110 comprises a microfluidic channel through which each cell 1 flows in order to align each cell 4 along its major axis. Each cell 4 inside the microfluidic channel may move, e.g., at velocities of about 0.163 m/s. This corresponds to a flow rate of about 0.04 µl/s. The dimensions of the microfluidic channel may be constructed in such a way that the diameters of the cells 4 are preferable 30% to 90% of the width of the microfluidic channel at the narrowest point of the microfluidic channel.

By ensuring the dimensions of the microfluidic channel with regard to the cell sizes as stated above, the cells 4 are deformed, i.e. extended along their major axis, due to the forces being present in the microfluidic channel and being applied on the cells 4. By extending the cells 4 along their ma or axis, cell attributes become visible which can be used for classification. If, however, the cells 4 are less than 30% of the width of the microfluidic channel, the forces applied on the cells 4 due to the microfluidic channel may be too small and not enough cell attributes of the cells 4 become visible that are needed for successful and correct classification. If, on the other side, the cells 4 cover more than 90% of the width of the microfluidic channel, the cells 4 may rub against the walls of the microfluidic channel also resulting in a less successful classification. Thus, it is preferred to ensure that the diameter of the cells 4 is 30% to 90% of the width of the microfluidic channel. For example, the width of the microfluidic channel may be 30 µm, more preferably 20 µm, in order to ensure successful and correct classification of cells having a size of, for example, 12-15 µm.

The channel can have a cross-sectional diameter of between 1 to 100 µm and preferably has a cross-sectional diameter of 50 µm or less. With smaller channels, it is difficult to allow cells to pass through them. With larger channels, the alignment effect is not as pronounced. The channels typically have a quadratic, rectangular or circular cross-sectional shape. The flow speed of the liquid carrying the cells is typically within the range of from 0.025 to 0.5 m/s, but can also range from 0.01 to 5.0 m/s. The material to be used for the channels is not particularly limiting as long as it is capable of allowing for imaging the cells 4 to be classified. I.e., the channel has to have enough transparency to allow for imaging. In prototypes, the channels were formed using PDMS (polydimethylsiloxane) on glass. From a manufacturing point of view, it is advantageous if a plastic material is used which can be molded. For the piezo elements to sort the cells, lithium niobate (LiNbO$_3$) was used which was covered first with silicon dioxide (i.e. glass) and then with PDMS. It was found that a silicon dioxide covering improves the adhesive properties of PDMS. The material forming the channel was not coated.

Once the cell 4 being present in the alignment unit 110 is aligned and extended along its major axis, an imaging unit 140 obtains an image of the cell 4 to be classified. The imaging unit 140 may be part of the classifying device 100 as described above. However, the imaging unit 140 may also not be part of the classifying device 100 and may transmit the image of the cell 4 to the classifying device 100 over a wired or wireless connection. In this case, the classifying device 100 may comprise a receiving unit being capable of receiving the image transmitted from the imaging unit 140. Irrespective of whether the imaging unit 140 is part of the classifying device 100 or not, the imaging unit 140 may comprise any common camera or image-capturing device which is capable of obtaining images of the cells 4. For example, the imaging unit 140 comprises a microscope (e.g. the Axiovert 200M (Zeiss, Oberkochen) equipped with a Plan-NEOFLUOAR® 40× NA 0.75 objective lens (Zeiss, Oberkochen)), a light source and a high-speed camera (MC1362 CMOS camera (Mikrotron, Unterschleissheim)) for capturing cell images. The cell images may be bright-field images of the cells 4.

Whilst it is preferred to have such an imaging unit, it would also be possible to run the classification method also on recorded images (e.g. a video or photographs of cells). That is, one does not, strictly speaking, need to have an imaging unit 140 as part of the apparatus.

After having obtained an image of the cell 4, the image is used by the MLP 130 described in much detail above in order to classify the cell 4. By using the MLP 4, i.e. a neural network, in this setup, the cell image can be classified in real-time and the classification result can be sent to the sorting unit 310 in less than 1 ms resulting in a fast and efficient classification and sorting process.

The sorting unit 310 may receive the classification result and may sort the corresponding cell 4 to the target outlet 400 or to the default outlet 500. For example, the sorting unit 310 uses standing or travelling surface waves within the acoustic wavelength range in order to separate the classified cells 4 and direct the classified cells 4 to the target outlet 400 and the default outlet 500 using the corresponding channels. However, the sorting unit 310 may also use any other technique for separating the cells 4. As a result, the chequered cells (e.g. white blood cells) are pushed to the target outlet 400 and the striped cells (e.g. red blood cells) are pushed to the default outlet 500. In another embodiment, instead of pushing the cells to the default outlet 500, the flow rates in the setup may be calibrated in such a way that all cells go by default into the default outlet 500, i.e. travel with the flow into the default outlet 500. If a cell is then classified as target cell, the target cell is pushed to the target outlet 400. To refer again to the example regarding the chequered cells and striped cells, the chequered cells may be pushed to the target outlet 400, while the striped cells may travel with the flow into the default outlet 500.

By using any one of the devices or setups described in detail above with reference to FIGS. 1 to 4, image processing of images, like bright-field images or any other images of cells, in real-time (approx. 200 µs per image) for cell classification and sorting is possible which corresponds to an acceleration of image processing of a factor of 100 compared to the state-of-the-art. With a setup similar to FIG. 4, 100 cells per second and up to 2000 cells per second can be classified depending on the flow rate of the cells. The flow rate of the cells may be adjusted accordingly to ensure both fast and correct classification. If the flow rate of the cells, however, is too high, it may be difficult to ensure correct classification. Thus, a balance has to be found between fast classification and correct classification of cells.

Cell classification may be performed on a common computing device, wherein real-time cell classification is achieved by first aligning the cells along their major axis, thus enabling image processing with standardized images, and then using an MLP for image analysis and classification. This results in a significant simplification and acceleration of the classification process. In addition, the cells may be deformed and extended along their major axis in the alignment unit and can thus be classified and sorted according to their mechanical properties which become visible on the cell images.

Figure 5:
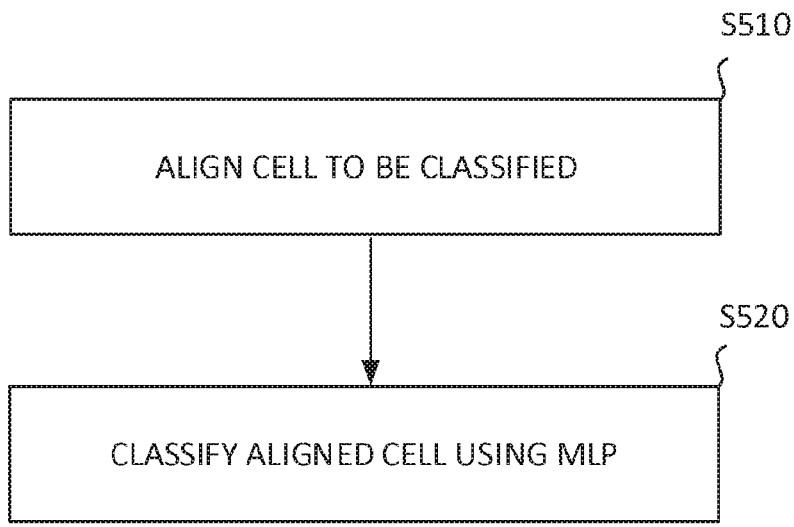
FIG. 5 illustrates a flowchart showing steps of a classifying method according to an embodiment of the present invention.

FIG. 5 illustrates a flowchart showing steps of a classifying method according to an embodiment of the present invention. The classifying method may be performed by the classifying device 100 described in more detail above with reference to FIGS. 1 to 4.

As illustrated in FIG. 5 the classifying method comprises step S510 for aligning a cell to be classified along the cell's major axis. Step S510 may be performed by the alignment unit 110 of the classifying device 100 as described above. For example, the cell to be classified flows through a microfluidic channel for alignment. In this matter, the diameter of the cell to be classified may preferably cover 30% to 90% of the width of the microfluidic channel. As explained above, by ensuring that the cell covers 30% to 90% of the microfluidic channel in width, the cell is deformed and extended along its major axis due to the forces being present in the microfluidic channel and being applied on the cell. Thus, its mechanical properties become visible on the cell image and cell classification based on cell images can be improved. Whilst presently, only one image of a cell is imaged, it is also possible to use more than one image of the cell for the classification using the MLP. For example, a video may be fed to the MLP. Given that such a video (which is a series of sequential images of the cell to be classified) could also include information regarding the mechanical properties such as the viscoelastic properties of the cell (due to imaging the cell when the cell is subjected to forces), classifying a cell based on such a video would be advantageous, since the amount of information is higher.

Then, in step S520 of the classifying method, the aligned cell is classified using an MLP, wherein the MLP classifies the aligned cell based on an image of the aligned cell. The MLP may have been trained on an input-output pair, the input being images of cells and the output being corresponding classification results. The structure and functions of the MLP has been explained in great detail above with reference to FIGS. 1 to 4, such that a detailed description of the MLP is omitted at this point for conciseness reasons.

In addition, the classifying method may comprise a step of obtaining the image of the aligned cell to be classified (not shown). The image of the cell used for classification may be a bright-field image or any other type of image showing the cell to be classified. In order to ensure a label-free classification in real-time, the cell to be classified is a marker-free cell. Thus, the disadvantages of labelling may be avoided.

Figure 6:
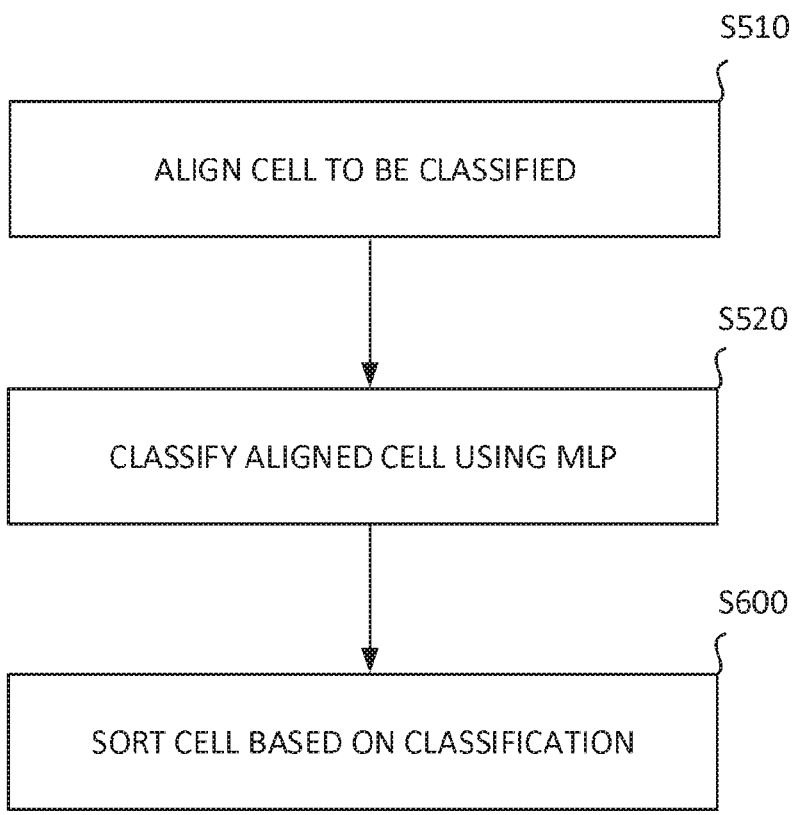
FIG. 6 illustrates a flowchart showing steps of a sorting method according to another embodiment of the present invention.

FIG. 6 illustrates a flowchart showing steps of a sorting method according to another embodiment of the present invention. The sorting method may be performed by the sorting device 300 as explained in more detail above with reference to FIGS. 1 to 4.

As illustrated in FIG. 6, the sorting method may comprise the steps S510 and S520 of the classifying method as described with reference to FIG. 5. A detailed description of steps 510 and S520 is omitted at this point for conciseness reasons.

In addition, the sorting method may comprise step S600 of sorting the classified cell to a target outlet or to a default outlet based on a classification result of the classifying method. A detailed description of sorting cells has been given with reference to FIGS. 3 and 4.

Figure 7A:
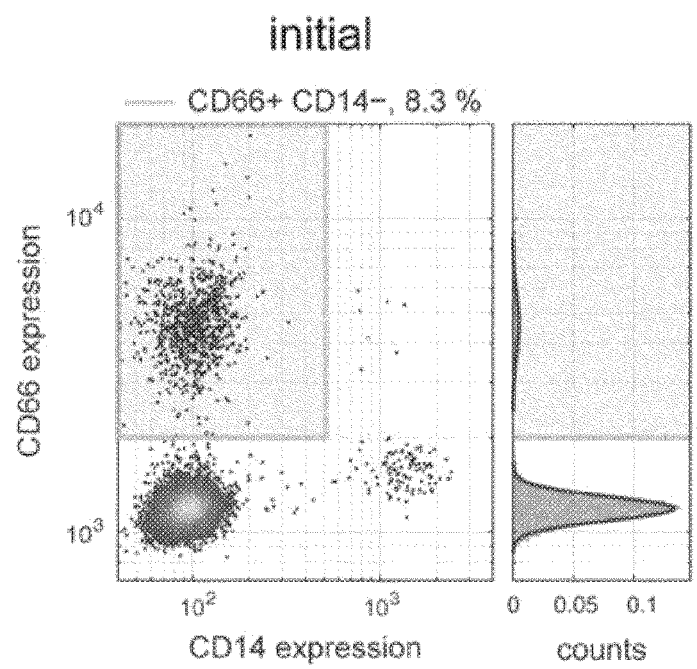
FIGS. 7A and 7B show exemplary measurement results of a heterogeneous sample, wherein the cell distributions before and after cell sorting using a multilayer perceptron are illustrated.
Figure 7B:
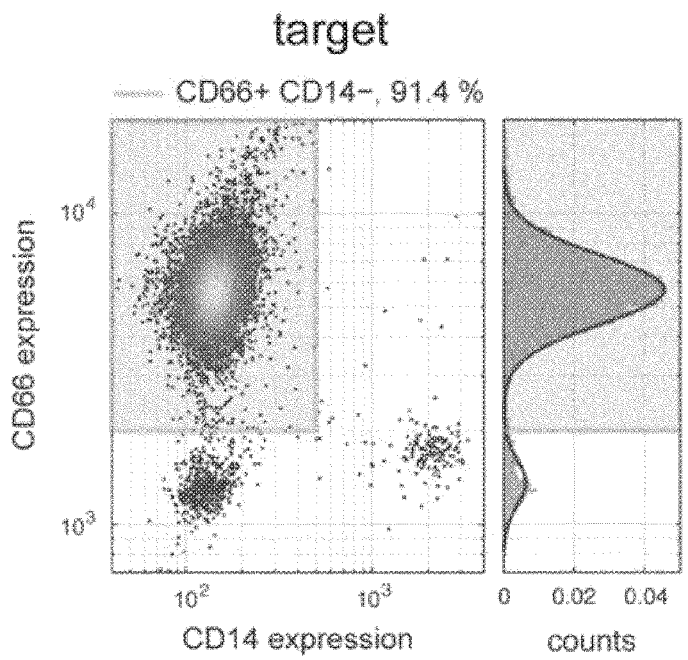

FIGS. 7A and 7B show exemplary measurement results of a heterogeneous sample, wherein the cell distributions before and after cell sorting using a multilayer perceptron are illustrated.

For FIGS. 7A and 7B, neutrophils are classified and sorted from red blood cell (RBC)-depleted blood (dextran sedimentation) using the sorting device 300 with an MLP. In this case, the input layer obtains images of 26×26 pixels resulting in 26×26=676 neurons in the input layer. Furthermore, the MLP includes three hidden layers, wherein the first hidden layer has 24 neurons, the second hidden layer has 16 neurons and the third hidden layer has 24 neurons. The output layer of the MLP comprises as many neurons as classes for classifying the cells. In this case, seven classes may be needed to classify thrombocytes (class 1), lymphocytes (class 2), red blood cells (class 3), doublets of red blood cells (class 4), monocytes (class 5), neutrophils (class 6), and eosinophils (class 7). Thus, due to seven classes, the output layer may comprise seven neurons. If only the white blood cells are of interest, the output layer may solely comprise two neurons referring to a first class for white blood cells and to a second class for the remaining cells. As an activation function, a rectifier is chosen.

In this matter, FIG. 7A shows the cell distribution of the initial sample before sorting and FIG. 7B shows the cell distribution after sorting the cells in the initial sample. The post-analysis of the target as well as the initial sample are performed using RT-FDC ("real time fluorescence and deformability cytometry") and CD14, CD66 staining. When comparing the scatterplots of FIGS. 7A and 7B, the scatterplots show a clear enrichment of CD66+ cells in the target. CD66+ cells (neutrophils) are clearly enriched in the target sample which means that CD66+ have been successfully separated from the (unwanted) CD14+ cells (monocytes)) and CD66−/CD14− cells (red blood cells). Thus, by using the cell classification and sorting as described with reference to FIGS. 1 to 6, it is possible to successfully collect CD66+ cells in the target outlet.

By executing the classifying and sorting devices or by performing the classifying and sorting methods as described above, an improved, efficient, and accurate classification and sorting of cells in real-time based on images of the cells with high throughput can be provided. Different cell types can be successfully classified and separated without cell labelling based only on their optical appearances. Since no labelling of the cells is necessary, staining procedures which can be time-consuming, expensive and have further side effects are not necessary. Label-free classification and sorting of cells may be essential for cell therapeutic and clinical applications.

The classifying and sorting devices/methods herein are not limited to these scenarios as described in detail above. As described above, embodiments and examples of the invention allow for improved classification and sorting based on cell images of cells with high throughput.

It will be appreciated that various modifications and variations can be made in the described systems and methods as well as in the construction of this invention without departing from the scope or spirit of the invention.

The invention has been described in relation to particular embodiments and examples which are intended in all aspects to be illustrative rather than restrictive.

Moreover, other implementations of the invention will be apparent to the skilled person from consideration of the specification and practice of the invention disclosed herein. It is intended that the specification and the examples be considered as exemplary only. To this end, it is to be understood that inventive aspects lie in less than all features of the foregoing disclosed implementation or configuration. Thus, the true scope of the invention is indicated by the following claims.

The invention claimed is:

1. A classifying device for classifying cells in real-time, the classifying device comprising:
   an alignment unit configured to align a cell to be classified, along the cell's major axis, prior to being imaged by an imaging unit, wherein the alignment unit is further configured to deform and extend the cell along the cell's major axis during alignment; and
   a classifying unit configured to classify the so-aligned deformed and extended cell using a multilayer perceptron, MLP, wherein the MLP has been trained based on a plurality of images of- aligned deformed and extended cells;
   wherein the MLP classifies the so-aligned deformed and extended cell based on one or more images of the- aligned deformed and extended cell.

2. The classifying device according to claim 1, wherein a cross-sectional diameter of the alignment unit is less than 100 μm.

3. The classifying device according to claim 2, a cross-sectional diameter of the alignment unit is less than 50 μm.

4. The classifying device according to claim 1, further comprising the imaging unit configured to obtain the one or more images of the- aligned deformed and extended cell to be classified.

5. The classifying device according to claim 1, wherein the alignment unit comprises a microfluidic channel through which the cell to be classified flows.

6. The classifying device according to claim 1, wherein the MLP has been trained on an input-output pair, the input being the plurality of images of the- aligned deformed and extended cells and the output being corresponding classification results, wherein the one or more images of the-aligned deformed and extended cell used for classification are images of a marker-free cell.

7. The classifying device according to claim 1, wherein the one or more images of the-aligned deformed and extended cell used for classification are bright-field images.

8. A sorting device comprising the classifying device of claim 1, further comprising a sorting unit configured to sort the classified cell to a target outlet or to a default outlet based on a classification result output by the classifying device.

9. The classifying device according to claim 5, wherein the alignment unit corresponds to a narrowing portion of the microfluidic channel.

10. The classifying device according to claim 1, wherein the alignment unit is configured to cause the cells flowing therein to align, deform and extend along their major axis.

11. A classifying method for classifying cells in real-time, comprising the steps of:
   aligning a cell to be classified, along the cell's major axis, prior to being imaged by an imaging unit;
   deforming and extending the cell along the cell's major axis during aligning, prior to being imaged by an imaging unit and classifying the so- aligned deformed and extended cell using a multilayer perceptron, MLP;
   wherein the MLP classifies the so- aligned deformed and extended cell based on one or more images of the so- aligned deformed and extended cell, wherein the MLP has been trained based on a plurality of images of- aligned deformed and extended cells.

12. The classifying method according to claim 11, wherein the cell to be classified flows through a microfluidic channel for alignment.

13. The classifying method according to claim 12, wherein the diameter of the cell to be classified is 30% to 90% of the minimum width of the microfluidic channel.

14. The classifying method according to claim 11, further comprising the step of obtaining, by the imaging unit, the one or more images of the so- aligned deformed and extended cell to be classified.

15. The classifying method according to claim 11, wherein the MLP has been trained on an input-output pair, the input being the plurality of images of- aligned deformed and extended cells and the output being corresponding classification results.

16. The classifying method according to claim 11, wherein the cell to be classified is a marker-free cell and/or wherein the one or more images of the cell used for classification are bright-field images.

17. A sorting method comprising the steps of the classifying method of claim 11, further comprising the step of sorting the classified cell to a target outlet or to a default outlet based on a classification result of the classifying method.

* * * * *